United States Patent
Abiko et al.

(10) Patent No.: US 6,726,739 B2
(45) Date of Patent: Apr. 27, 2004

(54) METHOD OF TREATING METAL ANALYSIS SAMPLE AND DEVICE THEREOF

(75) Inventors: Kenji Abiko, 27-9, Takamori 6-chome, Izumi-ku, Sendai-shi, Miyagi 981-3203 (JP); Hisao Yasuhara, Chiba (JP); Takashi Niida, Shinagawa (JP); Makoto Shimura, Chiba (JP); Hideo Iwai, Chigasaki (JP)

(73) Assignees: JFE Steel Corporation, Tokyo (JP); Japan Analyst Corporation, Tokyo (JP); Kenji Abiko, Miyagi (JP); Ulvac-Phi Incorporated, Kanagawa (JP)

(*) Notice: Subject to any disclaimer, the term of this patent is extended or adjusted under 35 U.S.C. 154(b) by 44 days.

(21) Appl. No.: 10/181,912

(22) PCT Filed: Oct. 11, 2001

(86) PCT No.: PCT/JP01/08932
§ 371 (c)(1),
(2), (4) Date: Jul. 24, 2002

(87) PCT Pub. No.: WO02/31493
PCT Pub. Date: Apr. 18, 2002

(65) Prior Publication Data
US 2003/0010633 A1 Jan. 16, 2003

(30) Foreign Application Priority Data
Oct. 12, 2000 (JP) ................................. 2000-311479

(51) Int. Cl.[7] ................................................ G01N 1/28
(52) U.S. Cl. ................... 75/10.12; 75/384; 204/192.33; 204/298.32; 266/79
(58) Field of Search ............. 204/192.33, 298.32; 75/384, 10.12; 266/79

(56) References Cited

FOREIGN PATENT DOCUMENTS

| JP | U 60-174397 | 11/1985 |
|---|---|---|
| JP | A 62-83953 | 4/1987 |
| JP | A 1-308939 | 12/1989 |
| JP | A 8-211043 | 8/1996 |
| JP | A 11-316220 | 11/1999 |

OTHER PUBLICATIONS

Patent Abstract of Japan Publication No. 11–316220 Date of publication of application Nov. 16, 1999.*
Hisao Yasuhara et al., "Influence of Sample Treatment Methods on the Determination of Trace Oxygen in Iron and Steel", The Iron and Steel Institute of Japan, vol. 85, pp 138 (1999).

* cited by examiner

*Primary Examiner*—Melvyn Andrews
(74) *Attorney, Agent, or Firm*—Oliff & Berridge, PLC

(57) ABSTRACT

The present invention provides a pre-treatment apparatus for an analytical metal sample, the apparatus including (1) a treatment chamber having a sample charging port which can be opened and closed and provided at the top of the chamber, a sample discharging port which can be opened and closed and provided at the bottom of the chamber, and a gas inlet and gas outlet, (2) a sample carrying bar joined to a sample holder also used as a sputtering electrode, and provided to pass through at least one side wall of the treatment chamber so as to be substantially horizontally movable and axially rotatable, and (3) a sputtering counter electrode at least having portions arranged opposite to each other in a region not inhibiting the charge and discharge of an analytical metal sample so that the sample holder can be arranged in the counter electrode. The present invention also provides a pre-treatment method capable of simply cleaning the surface of the analytical metal sample by using the pre-treatment apparatus and preventing re-contamination of the cleaned sample by exposure to the air or the like. Furthermore, the present invention provides an analysis apparatus provided with the pre-treatment apparatus to permit high-accuracy quantitative determination of trace elements of metals.

9 Claims, 1 Drawing Sheet

METHOD OF TREATING METAL ANALYSIS SAMPLE AND DEVICE THEREOF

TECHNICAL FIELD

The present invention relates to a method and apparatus for pre-treating a metal sample (referred to as an "analytical metal sample" hereinafter) subjected to metal analysis. Particularly, the present invention relates to a pre-treatment method and pre-treatment apparatus for removing contaminants adhering to and/or adsorbed on the surface of a metal sample before analysis of trace elements in a metal. Also, the present invention relates to an apparatus comprising the pre-treatment apparatus, for analyzing elements in a metal.

BACKGROUND ART

The trace elements of steel, for example, oxygen, carbon, nitrogen, and sulfur influence the material properties of steel, such as ductility, processability, etc., and accurate quantitative analysis is required. This is generally widely indicated in the fields of iron and steel industry and metal material industry with increases in purity of metal materials. Therefore, an apparatus and method for analyzing the elements in a metal with high accuracy and high operationality is required.

In order to comply with this requirement, the contaminants produced on the surface of an analytical metal sample must be removed in the step of preparing the sample. For example, when organic materials are adsorbed on the surface of the sample, or surface oxidation occurs by an atmosphere of carbon dioxide gas, air or the like, oxygen analysis of steel causes significant error in the analytical value. Therefore, in a melting-infrared absorption method in an inert gas, which is widely used as an analysis method for trace oxygen in a metal, the surface of the analytical metal sample is cleaned by an electropolishing method or chemical polishing method before analysis. This method can remove most of the surface contaminants. However, actually, the surface of the analytical metal sample is again contaminated with the chemicals used for cleaning and polishing, and the contaminants removed, or again oxidized by the air before measurement by an analysis apparatus. For example, in quantitative analysis of oxygen, the influence of such residual contamination and re-contamination on the analytical value corresponds to 1 to 2 ppm in terms of concentration, and causes error in a ppm level (Iron and Steel, Vol. 85, p. 138(1999), etc.). Particularly, on the clean surface of a metal, adsorption of atmospheric materials, oxidization, or the like momentarily occurs, and it is thus important for improving analysis accuracy to remove a re-contaminated portion or a portion contaminated with residual materials.

Under the above background, Japanese Unexamined Patent Application Publication No. 8-211043 discloses a method in which an electric discharge is induced in an analytical metal sample in a low-pressure gas to remove contaminants from the surface, and then transferred to an analysis apparatus for analyzing carbon. This electric discharge cleaning is referred to as "sputtering treatment".

However, in the method disclosed in Japanese Unexamined Patent Application Publication No. 8-211043, one counter electrode is used for the electric discharge of the metal sample, and a sample support on which the metal sample is mounted has a plate form. Therefore, in order to clean the back side of the sample (the surface in contact with the sample support) by sputtering, the analytical metal sample must be rotated or reversed. However, the operation of reversing the sample is complicated, and the operation is likely to again bring the analytical metal sample into contact with the air or drop the sample from the sample support. When the sample drops from the sample support, analysis can no longer be performed. Therefore, in the method disclosed in Japanese Unexamined Patent Application Publication No. 8-211043, in fact, the back side (in contact with the sample support) of the metal sample, which occupies a large area, cannot be cleaned by sputtering.

Japanese Unexamined Patent Application Publication No. 11-316220 discloses a method in which an analytical metal sample is sputtered in an inert atmosphere in a pre-treatment chamber connected to an analysis apparatus, and then the sample from which contaminants are removed from the surface is moved to an elementary analysis apparatus without being exposed to the air. In this method, the side of the metal sample is point-supported, and thus contaminants can be simultaneously removed from almost the whole area of the surfaces of the analysis sample.

However, the analytical metal sample is point-supported to cause difficulties in setting the analytical sample, and a great problem of operationality remains.

An object of the present invention is to provide a pre-treatment apparatus and pre-treatment method which can resolve the problems of the conventional techniques, and can effectively remove contaminants from the surface of a metal sample in order to improve the accuracy of quantitative analysis of trace components of a metal. Another object of the present invention is to provide an analysis apparatus comprising the pre-treatment apparatus.

DISCLOSURE OF INVENTION

The present invention provides an apparatus for pre-treating an analytical metal sample, comprising (1) a treatment chamber having a sample charging port which can be opened and closed and provided at the top of the chamber, a sample discharging port which can be opened and closed and provided at the bottom of the chamber, and a gas inlet and gas outlet, (2) a sample carrying bar connected to a sample holder also used as a sputtering electrode, and provided to pass through at least one side wall of the treatment chamber so as to be substantially horizontally movable and axially rotatable, and (3) a sputtering counter electrode at least having portions arranged opposite to each other in a region not inhibiting the charge and discharge of the analytical metal sample so that the sample holder can be arranged in the counter electrode.

In the pre-treatment apparatus, the contact area between the sample and the sample holder is preferably 10% or less of the surface area of the analytical metal sample.

In the pre-treatment apparatus, the counter electrode at least having portions arranged opposite to each other preferably has a cylindrical shape.

The present invention also provides an elementary analysis apparatus for a metal, comprising a sample inlet port connected to a portion below the sample discharging port of the pre-treatment apparatus.

The present invention further provides a pre-treatment method for elementary analysis of a metal using the pre-treatment apparatus, comprising the steps of (1) charging an analytical metal sample in the sample holder through the sample charging port, (2) evacuating the treatment chamber to form a reduced pressure atmosphere, and then controlling the inside of the treatment chamber to a predetermined pressure of 100 Pa to 1000 Ps by using an inert gas, (3)

moving the analytical metal sample on the sample holder by the sample carrying bar to a position in the sputtering counter electrode at least having portions opposite to each other, (4) applying a voltage between the sample-side electrode and the sputtering counter electrode to clean the surface of the analytical metal sample by sputtering, (5) moving the sample holder to a position above the sample discharging port by the sample carrying bar, (6) rotating the sample carrying bar to move the analytical metal sample to an elementary analysis apparatus through the sample discharging port.

BEST MODE FOR CARRYING OUT THE INVENTION

As disclosed in the claims, the present invention can be roughly divided into the three inventions including a pre-treatment apparatus and a pre-treatment method for an analytical metal sample, and an elementary analysis apparatus for a metal comprising the pre-treatment apparatus. In order to facilitate understanding of the present invention, the pre-treatment apparatus and the elementary analysis apparatus comprising the same are described with reference to an embodiment, and the pre-treatment method is described with reference to an embodiment.

The pre-treatment method of the present invention can be preferably applied to a pre-treatment method in which the surface of an analytical metal sample is cleaned by sputtering in a treatment chamber maintaining an inert gas atmosphere before analysis of the component elements of a metal, as disclosed, for example, in Japanese Unexamined Patent Application Publication No. 11-316220. In Japanese Unexamined Patent Application Publication No. 11-316220, the side of the analytical metal sample is supported at two points. However, the present invention is characterized in that the bottom of the analytical metal sample is supported by the sample holder, and the contact area between the sample and the sample holder is decreased as much as possible.

Figure 1:
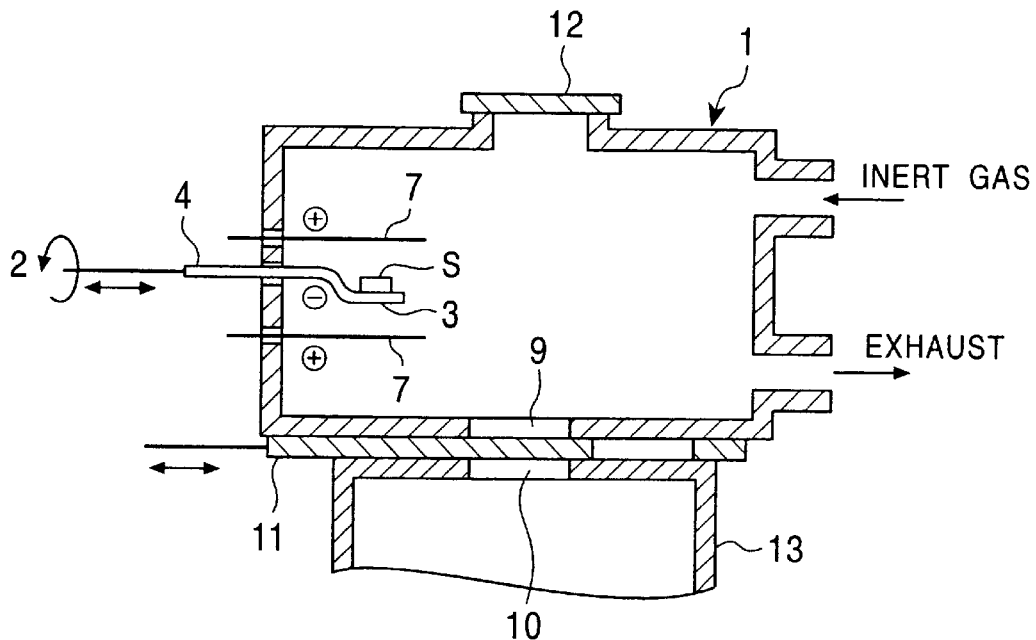
FIG. 1 is a drawing illustrating a metal analysis apparatus comprising a pre-treatment apparatus for an analytical metal sample according to an embodiment of the present invention.

FIG. 1 is a drawing illustrating a pre-treatment apparatus for an analytical metal sample according to an embodiment of the present invention. As shown in FIG. 1, in the present invention, like in the conventional example disclosed in Japanese Unexamined Patent Application Publication No. 11-316220, contaminants of the surface of an analytical metal sample S are removed by sputtering in a treatment chamber 1, and then the sample S is introduced into an elementary analysis apparatus 13.

The treatment chamber 1 preferably comprises a casing having an inert gas inlet and inert gas outlet, and a sample charging port 12 provided at the top of the body and a sample discharging port 9 provided at the bottom of the body. The sample discharging port 9 is connected to a sample inlet port 10 of the elementary analysis apparatus 13.

In the treatment chamber 1, a sample holder 3 also functioning as a sputtering cathode is provided, the sample holder 3 being joined to a sample carrying bar 4. The carrying bar 4 passes through the side wall of the treatment chamber 1 to be connected to a movement and rotation mechanism 2 in the outside. Consequently, the analytical metal sample S mounted on the sample holder 3 can be moved substantially horizontally in the transverse direction, and the carrying bar 4 can be reversed at a predetermined position to drop the analytical metal sample from the sample holder. Furthermore, in the treatment chamber 1, sputtering anodes 7 are disposed opposite to each other in a region not inhibiting the charge and discharge of the analytical metal sample S. The opposite anodes 7 are disposed so that the sample holder 3 on which the analytical metal sample S is mounted can be arranged between the anodes 7. The sample holder 3 and the anodes 7 are connected to a power supply (not shown in the drawing) generating a high voltage, for example, of 1 KV.

The analytical metal sample S is charged in the sample holder 3 through the sample charging port 12 by using the pre-treatment apparatus. Next, the charging port 12 and a slide gate 11 are closed, and the inside of the treatment chamber 1 is evacuated. Then, the inside is controlled to predetermined pressure in the range of 100 Pa to 1000 Pa by using an inter gas, for example, an argon gas. Then, the analytical metal sample S mounted on the sample holder 3 is horizontally moved to the space between the opposite anodes 7 by the sample carrying bar 4. In this state, a voltage is applied between the sample holder 3 (cathode) and the counter electrodes 7 (anodes) to remove contaminants from the surface of the analytical metal sample S by sputtering. Then, the sample holder 3 on which the cleaned sample S is mounted is moved to a position above the sample discharging port 9 by the sample carrying bar 4, and then the slide gate 11 is opened. Then, the sample carrying bar 4 is rotated to drop the analytical metal sample S into the elementary analysis apparatus through the sample inlet port 10 of the elementary analysis apparatus. Then, elementary analysis is performed.

An electric discharge (sputtering) can also be induced by reversing the polarities, i.e., using the sample holder 3 as an anode, and the counter electrodes 7 as cathodes.

Figure 2:
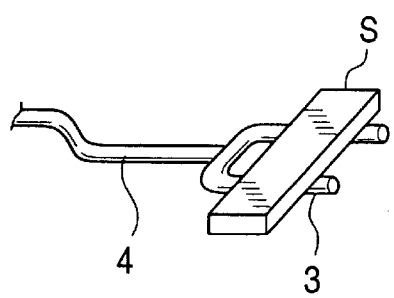
FIG. 2 is a perspective view showing an example of a state in which an analytical metal sample is mounted on a sample holder according to the present invention.

In the present invention, the analytical metal sample S can be supported by the sample holder 3 comprising two bars, as shown in FIG. 2. In this case, the analytical metal sample S is supported while being mounted on the sample holder 3, and has the small area of contact with the bottom of the sample holder 3. As a result, not only the top face and the side face of the analytical metal sample S but also the bottom face except only the small area of contact with the supporting portion 3 can be sputtered. Furthermore, there is the property that sputtering wraparoundly reaches the analytical metal sample S serving as an electrode, and thus contaminants can be removed from almost the whole area of the surface of the sample S. Furthermore, the work of charging and installing the sample comprises simply mounting the sample on the supporting portion 3, and thus the work can easily and stably be carried out.

In order to achieve the above function, it is necessary that the sample holder 3 supports the bottom of the analytical metal sample 3, the area of the sample holder in contact with the bottom of the analytical metal sample S is very small, and a sufficient space is secured for collision of sputtering ions (for example, argon ions) with the bottom of the analytical metal sample S at a high speed.

Figure 3:
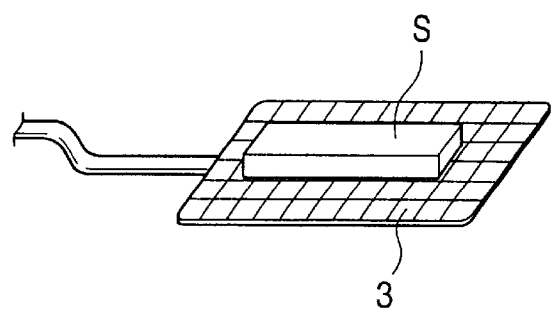
FIG. 3 is a perspective view showing another example of a state in which an analytical metal sample is mounted on a sample holder according to the present invention.

Another example of the shape of the sample holder 3 used in the present invention is such a wire-net shape as shown in FIG. 3. Other shapes such as a rectangular or circular frame shape and the like can also be used as long as the area of contact with the bottom of the analytical metal sample S is small and a large space is formed, as viewed from the counter electrodes 7. The area of contact between the analytical metal sample S and the sample holder 3 is preferably designed to be as small as possible because analysis error is greatly affected by the rate of removal of surface contaminants. The area of the sample holder, which is in contact with the sample, is preferably 10% or less of the surface area of the analytical metal sample S. The contact area is more preferably 5% or less of the bottom area of the analytical metal sample, and most preferably 3% or less of the bottom area of the analytical metal sample.

Since the sample holder 3 functions to maintain the analytical metal sample S in a predetermined polarity state during removal of surface contaminants by sputtering, the sample holder 3 preferably has excellent electric conductivity. Also, the sample holder 3 should be selected so that contaminants such as gases are not produced by the heat generated in sputtering. From this viewpoint, for example, 18-8 stainless steel is preferably used.

In the pre-treatment apparatus of the present invention, the sample holder 3 is provided in the treatment chamber 1 so that it can be moved backward and forward and can be rotated. In the embodiment shown in FIG. 1, the sample holder 3 is connected to the movement and rotation mechanism 2 through the sample carrying bar 4 so that the sample holder 3 is moved forward and backward and rotated in the treatment chamber 1 by the movement and rotation mechanism 2 using known means such as a motor, a cylinder, or the like.

In the present invention, "a region not inhibiting the charge and discharge of the analytical metal sample in the treatment chamber" which is defined as the setting position of the counter electrode, is, for example, a region other than the vertical regions adjacent to both the charging port 12 and the discharging port 9 shown in FIG. 1. However, in the present invention, the counter electrodes 7 (anodes) may be projected into the vertical region adjacent to the sample charging port 12 and/or the sample discharging port 9 as long as the counter electrodes 7 do not inhibit the charge and discharge of the sample. However, the analysis sample holder 3 is preferably set apart from the vertical region adjacent the sample charging port.

Furthermore, in the present invention, "a sputtering counter electrode at least having portions arranged opposite to each other" is described. In the embodiment shown in FIG. 1, the two counter electrodes 7 (anodes) are provided above and below the sample holder 3 (cathode) on which the analytical metal sample S is mounted. This is intended to clean the metal sample by sputtering from above and below. Therefore, "a counter electrode at least having portions arranged opposite to each other" may be provided so that the portions are opposite to each other in the vertical direction or in the transverse direction or oblique direction according to the shape of the sample. In the present invention, the counter electrode may be provided so that the portions are opposite to each other at unsymmetrical portions with respect to the analytical metal sample, but the counter electrode is generally preferably provided so that the portions are opposite to each other at symmetrical positions with respect to the metal sample because uniform sputtering causes less analytical error. From the viewpoint of uniform and efficient sputtering, a cylindrical counter electrode is preferably used so that the sample holder on which the metal sample is mounted is disposed in the cylindrical counter electrode. The cylindrical counter electrode may be, for example, rectangular or circular, but a circular cylinder is more preferable. Alternatively, a curved counter electrode may be used. As the curved counter electrode, a substantially cylindrical electrode formed by cutting off a portion of a cylindrical counter electrode may be used, or counter electrodes curved in a semicircle may be disposed opposite to each other. In this way, as the counter electrode, a plurality of plate-shaped counter electrodes or curved counter electrodes may be provided opposite to each other, or a substantially cylindrical or cylindrical counter electrode may be provided. Therefore, in the present invention, the counter electrode is defined as "a counter electrode at least having portions arranged opposite to each other".

The above-described pre-treatment apparatus and pre-treatment method are capable of effectively removing (sputtering) surface contaminants of the analytical metal sample S within a relatively narrow space surrounded by the counter electrodes 7.

The present invention can be applied to any analysis object metal regardless of the type of the metal, the type of the element to be analyzed and the analysis method used. Furthermore, the type of sputtering is not limited, and arc sputtering may be used. The analytical sample holder, the counter electrode and the periphery thereof may be cooled directly or indirectly with an appropriate cooling medium.

EXAMPLES

A steel sample of 6 mm φ×5 mm was used as an analytical metal sample, and the oxygen content of the steel sample was determined by a melting-infrared absorption method in an inert gas. The results are shown in Table 1. In Table 1, the results of an example were obtained by oxygen analysis after pre-treatment by the pre-treatment apparatus of the present invention shown in FIG. 1. On the other hand, the results of a comparative example were obtained directly from oxygen analysis without pre-treatment. In the table, X represents the average value of oxygen contents measured 5 times for each of two samples A and B, and σ represents the standard deviation (variation). These results indicate that in the example of the present invention, the analytical value of oxygen is about 1 to 2 ppm lower than that of the comparative example, and analysis accuracy is also improved. Also, as a result of surface analysis, the oxygen content corresponding to surface contaminants was estimated to about 1 to 2 ppm. Therefore, it is thought that surface contaminants can be removed by pre-treatment according to the present invention. Although the method disclosed in Japanese Unexamined Patent Application Publication No. 11-316220 has complication in charging an analytical metal sample, the method using the pre-treatment apparatus of the present invention comprises simply charging an analytical metal sample through the charging port, and can thus be performed by a very simple operation.

TABLE 1

| Sample | | Example | Comparative Example |
|---|---|---|---|
| A | X (ppm) | 15.8 | 17.5 |
|   | σ (ppm) | 0.22 | 0.30 |
| B | X (ppm) | 3.3 | 4.0 |
|   | σ (ppm) | 0.20 | 0.40 |

INDUSTRIAL APPLICABILITY

The pre-treatment apparatus and pre-treatment method of the present invention can simply perform pre-treatment for cleaning the surface of an analytical metal sample by sputtering while preventing re-contamination by exposure to the air. Also, an elementary analysis apparatus for metals comprising the pre-treatment apparatus of the present invention is less affected by surface contaminants of a metal to produce elementary analytical values with high accuracy, and requires a short time for pre-treatment of an analytical sample. Therefore, the present invention can rapidly and accurately evaluate the purities not only of steel materials but also of non-ferrous metal materials, etc., thereby permitting automation of a series of analysis works.

What is claimed is:

1. A pre-treatment apparatus for an analytical metal sample, the apparatus comprising:
   (1) a treatment chamber having a sample charging port which can be opened and closed and provided at the top of the chamber, a sample discharging port which can be opened and closed and provided at the bottom of the chamber, and a gas inlet and gas outlet;
   (2) a sample carrying bar joined to a sample holder also used as a sputtering electrode, and provided to pass through at least one side wall of the treatment chamber so as to be substantially horizontally movable and axially rotatable; and
   (3) a sputtering counter electrode at least having portions arranged opposite to each other in a region not inhibiting the charge and discharge of an analytical metal sample so that the sample holder can be arranged in the counter electrode.

2. A pre-treatment apparatus according to claim 1, wherein the sample contact area of the sample holder is 10% or less of the surface area of the analytical metal sample.

3. A pre-treatment apparatus according to claim 1, wherein the counter electrode at least having portions arranged opposite to each other has a cylindrical shape.

4. An elementary analysis apparatus for a metal, comprising a sample inlet port connected to a portion below the sample discharging port of the pre-treatment apparatus according to claim 1.

5. A pre-treatment method for elementary analysis of a metal using the pre-treatment apparatus according to claim 1, the method comprising the steps of:
   (1) charging an analytical metal sample in the sample holder through the sample charging port;
   (2) evacuating the treatment chamber to form a reduced pressure atmosphere, and then controlling the inside of the treatment chamber to a predetermined pressure of 100 Pa to 1000 Pa by using an inert gas;
   (3) moving the analytical metal sample on the sample holder by the sample carrying bar to a position in the sputtering counter electrode at least having portions opposite to each other;
   (4) applying a voltage between the sample-side electrode and the sputtering counter electrode to clean the surface of the analytical metal sample by sputtering;
   (5) moving the sample holder to a position above the sample discharging port by the sample carrying bar;
   (6) rotating the sample carrying bar to move the analytical metal sample to an elementary analysis apparatus through the open sample discharging port.

6. An elementary analysis apparatus for a metal, comprising a sample inlet port connected to a portion below the sample discharging port of the pre-treatment apparatus according to claim 2.

7. An elementary analysis apparatus for a metal, comprising a sample inlet port connected to a portion below the sample discharging port of the pre-treatment apparatus according to claim 3.

8. A pre-treatment method for elementary analysis of a metal using the pre-treatment apparatus according to claim 2, the method comprising the steps of:
   (1) charging an analytical metal sample in the sample holder through the sample charging port;
   (2) evacuating the treatment chamber to form a reduced pressure atmosphere, and then controlling the inside of the treatment chamber to a predetermined pressure of 100 Pa to 1000 Pa by using an inert gas;
   (3) moving the analytical metal sample on the sample holder by the sample carrying bar to a position in the sputtering counter electrode at least having portions opposite to each other;
   (4) applying a voltage between the sample-side electrode and the sputtering counter electrode to clean the surface of the analytical metal sample by sputtering;
   (5) moving the sample holder to a position above the sample discharging port by the sample carrying bar;
   (6) rotating the sample carrying bar to move the analytical metal sample to an elementary analysis apparatus through the open sample discharging port.

9. A pre-treatment method for elementary analysis of a metal using the pre-treatment apparatus according to claim 3, the method comprising the steps of:
   (1) charging an analytical metal sample in the sample holder through the sample charging port;
   (2) evacuating the treatment chamber to form a reduced pressure atmosphere, and then controlling the inside of the treatment chamber to a predetermined pressure of 100 Pa to 1000 Pa by using an inert gas;
   (3) moving the analytical metal sample on the sample holder by the sample carrying bar to a position in the sputtering counter electrode at least having portions opposite to each other;
   (4) applying a voltage between the sample-side electrode and the sputtering counter electrode to clean the surface of the analytical metal sample by sputtering;
   (5) moving the sample holder to a position above the sample discharging port by the sample carrying bar;
   (6) rotating the sample carrying bar to move the analytical metal sample to an elementary analysis apparatus through the open sample discharging port.

* * * * *